United States Patent
Yoshino et al.

(10) Patent No.: US 7,189,880 B2
(45) Date of Patent: Mar. 13, 2007

(54) PROCESS FOR PRODUCING 2,4'-DIHYDROXYDIPHENYLSULFONE

(75) Inventors: Gou Yoshino, Nyu-gun (JP); Yuichi Tomoda, Fukui (JP); Norihiro Taniguchi, Fukui (JP); Kazuaki Igarashi, Fukui (JP); Takeo Hasegawa, Sakai-gun (JP)

(73) Assignee: Nicca Chemical Co., Ltd., Fukui (JP)

( * ) Notice: Subject to any disclaimer, the term of this patent is extended or adjusted under 35 U.S.C. 154(b) by 425 days.

(21) Appl. No.: 10/500,997

(22) PCT Filed: Jan. 22, 2003

(86) PCT No.: PCT/JP03/00571

§ 371 (c)(1),
(2), (4) Date: Jul. 7, 2004

(87) PCT Pub. No.: WO03/062194

PCT Pub. Date: Jul. 31, 2003

(65) Prior Publication Data

US 2005/0049437 A1 Mar. 3, 2005

(30) Foreign Application Priority Data

Jan. 23, 2002 (JP) .............................. 2002-013992

(51) Int. Cl.
*C07C 315/06* (2006.01)
*C07C 315/00* (2006.01)

(52) U.S. Cl. ........................... 568/34; 568/28; 568/32; 568/33

(58) Field of Classification Search .................. 568/34, 568/28, 32, 33
See application file for complete search history.

(56) References Cited

U.S. PATENT DOCUMENTS

| 5,399,772 A | 3/1995 | Hosoda et al. |
| 5,767,318 A | 6/1998 | Hosoda et al. |

FOREIGN PATENT DOCUMENTS

| EP | 0627415 A1 | 12/1994 |
| GB | 2 088 858 A | 6/1982 |
| JP | 50-106936 A | 8/1975 |
| JP | 57-77667 A | 5/1982 |
| JP | 61-24559 A | 2/1986 |
| JP | 9-40635 A | 2/1997 |
| JP | 10-25277 A | 1/1998 |
| JP | 10-139756 A | 5/1998 |

OTHER PUBLICATIONS

English-language International Preliminary Examination Report dated Sep. 23, 2004 of International application No. PCT/JP03/00571 filed Jan. 22, 2003, Applicants: NICCA Chemical Co., Ltd. et al.

*Primary Examiner*—Elvis O. Price
(74) *Attorney, Agent, or Firm*—Frishauf, Holtz, Goodman & Chick, P.C.

(57) ABSTRACT

A process for producing 2,4'-dihydroxydiphenylsulfone which comprises separating 4,4'-dihydroxydiphenylsulfone by crystallization from a mixture containing 4,4'-dihydroxydiphenylsulfone, 2,4'-dihydroxydiphenylsulfone, phenolsulfonic acid and phenol which is obtained by dehydration of phenol and sulfuric acid or phenolsulfonic acid to obtain a mixture having a content of 2,4'-dihydroxydiphenylsulfone greater than the content of 4,4'-dihydroxydiphenylsulfone, crystallizing 2,4'-dihydroxydiphenylsulfone by adjusting the composition of the solvent of the obtained mixture so that the ratio of the amounts by weight of phenol to water is 10:90 to 90:10, and separating 2,4'-dihydroxydiphenylsulfone by filtration; and a process as described above in which the filtrate obtained by the filtration is used as the raw material for the hydration.

2 Claims, 2 Drawing Sheets

PROCESS FOR PRODUCING 2,4'-DIHYDROXYDIPHENYLSULFONE

This application is the United States national phase application of International Application PCT/JP03/00571 filed Jan. 22, 2003.

TECHNICAL FIELD

The present invention relates to a process for producing 2,4'-dihydroxydiphenylsulfone. More particularly, the present invention relates to a process for producing 2,4'-dihydroxydiphenylsulfone which comprises efficiently separating 2,4'-dihydroxydiphenylsulfone from a mixture comprising 4,4'-dihydroxydiphenylsulfone and 2,4'-dihydroxydiphenylsulfone and effectively utilizing phenolsulfonic acid contained in the reaction mixture as the raw material.

BACKGROUND ART

A mixture of 4,4'-dihydroxydiphenylsulfone and 2,4'-dihydroxydiphenylsulfone can be obtained by condensation with dehydration of phenol and sulfuric acid. 4,4'-Dihydroxydiphenylsulfone is known as the raw material for polyether sulfone which is an engineering plastic exhibiting excellent heat resistance and a monomer for improving heat resistance of polycarbonates. 2,4'-Dihydroxydiphenylsulfone is a useful compound which is used as a developer for heat-sensitive recording materials and, in particular, provides excellent heat-sensitive recording paper exhibiting excellent coloring property, causing little fog on the background and stored with stability.

The product of condensation with dehydration of phenol and sulfuric acid is a mixture of 4,4'-dihydroxydiphenylsulfone and 2,4'-dihydroxydiphenylsulfone. Therefore, it is necessary for obtaining highly pure 4,4'-dihydroxydiphenylsulfone or 2,4'-dihydroxydiphenylsulfone that these compounds are separated from each other. Various processes for the separation have been examined.

As for the process for separating 4,4'-dihydroxydiphenylsulfone, for example, a process in which a mixture of the isomers of dihydroxydiphenylsulfone is dissolved into phenol by heating, 4,4'-dihydroxydiphenylsulfone alone is separated by crystallization as an addition compound with phenol by cooling, and then crystals of 4,4'-dihydroxydiphenylsulfone are obtained by a treatment of heating, is proposed in Japanese Patent Application Laid-Open No. Showa 57(1982)-77667 as the process for separating a highly pure 4,4'-dihydroxydiphenylsulfone from a mixture of the isomers. In Japanese Patent Application Laid-Open No. Showa 50(1975)-106936, a process in which a product of the reaction between phenol and sulfuric acid is brought into contact with an aqueous solution of phenol having a concentration of 3 to 35% by weight, and 4,4'-dihydroxy-diphenylsulfone is separated by crystallization, is proposed as the process for producing 4,4'-dihydroxydiphenylsulfone having a small content of the isomer. However, in accordance with these processes, it is difficult that 2,4'-dihydroxydiphenylsulfone is separated from the residual mixture obtained after the separation of 4,4'-dihydroxydiphenylsulfone.

In Japanese Patent Application Laid-Open No. Heisei 10(1998)-25277, a process in which phenol and a sulfonating agent are brought into reaction in a solvent of o-dichlorobenzene, the amount of the unreacted phenol in the reaction mixture is adjusted to 2 to 20% by weight based on the total of the amounts of the unreacted phenol and o-dichlorobenzene, and the total of the amounts of the unreacted phenol and o-dichlorobenzene is adjusted to 2 to 7 times the theoretical yield of dihydroxydiphenylsulfones when the reaction is completed so that 4,4'-dihydroxydiphenylsulfone is separated by crystallization from the reaction mixture, and 2,4'-dihydroxydiphenylsulfone is isolated form the filtrate, is proposed as the process for producing a combination of highly pure 2,4'-dihydroxydiphenylsulfone and 4,4'-dihydroxydiphenylsulfone industrially advantageously. However, since this process uses the chlorine-based organic solvent, this process requires a facility for recovery of the solvent and, moreover, tends to cause problems on the environment.

In Japanese Patent Application Laid-Open No. Heisei 9(1997)-40635, a process in which, in an aqueous solution of a mixture of 2,4'-dihydroxydiphenylsulfone and 4,4'-dihydroxydiphenylsulfone, 2,4'-dihydroxydiphenylsulfone is dissolved as a dialkali metal salt and 4,4'-dihydroxydiphenylsulfone is separated as a monoalkali metal salt in the presence of a hydroxide of an alkali metal, is proposed as the process for efficiently producing highly pure 2,4'-dihydroxydiphenylsulfone. However, in accordance with this process, great amounts of sodium hydroxide and sulfuric acid are used for the separation, and the efficiency is small from the standpoint of the cost.

The present invention has an object of providing a process for efficiently and economically advantageously separating 2,4'-dihydroxydiphenylsulfone from a reaction mixture comprising 4,4'-dihydroxydiphenylsulfone and 2,4'-dihydroxydiphenylsulfone and effectively utilizing phenolsulfonic acid contained in the reaction mixture as the raw material.

DISCLOSURE OF THE INVENTION

As the result of intensive studies by the present inventors to overcome the above problems, it was found that, when a mixture of the isomers had a content of 2,4'-dihydroxydiphenylsulfone greater than the content of 4,4'-dihydroxydiphenylsulfone, 2,4'-dihydroxydiphenylsulfone was selectively separated by crystallization from a solvent containing phenol and water in amounts such that the ratio of the amounts by weight of phenol to water was in the range of 10:90 to 90:10, and the filtrate obtained after separation of the crystals by filtration could be effectively utilized as the raw material for producing dihydroxydiphenylsulfones. The present invention has been completed based on this knowledge.

The present invention provides:

(1) A process for producing 2,4'-dihydroxydiphenylsulfone which comprises separating 4,4'-dihydroxydiphenylsulfone by crystallization from a mixture comprising 4,4'-dihydroxydiphenylsulfone, 2,4'-dihydroxydiphenylsulfone, phenolsulfonic acid and phenol which is obtained by dehydration of phenol and sulfuric acid or phenolsulfonic acid so that a mixture having a content of 2,4'-dihydroxydiphenylsulfone greater than a content of 4,4'-dihydroxydiphenylsulfone is obtained, crystallizing 2,4'-dihydroxydiphenylsulfone by adjusting a composition of a solvent of an obtained mixture so that a ratio of an amount by weight of phenol to an amount by weight of water is in a range of 10:90 to 90:10, and separating 2,4'-dihydroxydiphenylsulfone by filtration; and (2) A process for producing 2,4'-dihydroxydiphenylsulfone described in (1), which comprises adding phenol and sulfuric acid to a filtrate obtained by the separation of 2,4'-dihydroxydiphenylsulfone by filtration, conducting dehydration using a resultant mixture, separating 4,4'-dihydroxydiphenylsulfone by crystallization from a product of dehydration comprising 4,4'-dihydroxydiphenylsulfone, 2,4'-dihydroxydiphenylsulfone, phenolsulfonic acid and phenol so that a mixture having a content of 2,4'-dihydroxydiphenylsulfone greater than a content of 4,4'-dihydroxydiphenylsulfone is obtained, crystallizing 2,4'-dihydroxydiphenylsulfone by adjusting a composition of a solvent of an obtained mixture so that a ratio of an amount by weight of phenol to an amount by weight of water is in a range of 10:90 to 90:10, and separating 2,4'-dihydroxydiphenylsulfone by filtration.

THE MOST PREFERRED EMBODIMENT TO CARRY OUT THE INVENTION

In the process for producing 2,4'-dihydroxydiphenylsulfone of the present invention, 4,4'-dihydroxydiphenylsulfone is separated by crystallization from a mixture comprising 4,4'-dihydroxydiphenylsulfone, 2,4'-dihydroxydiphenylsulfone, phenolsulfonic acid and phenol which is obtained by dehydration of phenol and sulfuric acid or phenolsulfonic acid, and a mixture having a content of 2,4'-dihydroxydiphenylsulfone greater than the content of 4,4'-dihydroxydiphenylsulfone is obtained. 2,4'-Dihydroxydiphenylsulfone is crystallized by adjusting the composition of the solvent of the obtained mixture so that the ratio of the amount by weight of phenol to the amount by weight of water is in the range of 10:90 to 90:10, and the crystals of 2,4'-dihydroxydiphenylsulfone are separated by filtration.

A reaction mixture comprising 4,4'-dihydroxydiphenylsulfone and 2,4'-dihydroxydiphenylsulfone can be obtained by mixing phenol and sulfuric acid and/or phenolsulfonic acid, followed by heating the resultant mixture and removing formed water by distillation as an azeotrope. It is preferable that the reaction is conducted under a reduced pressure. It is preferable that, where necessary, phenol is added during the reaction to supplement phenol removed to the outside of the system by the azeotropic distillation with water. In general, 4,4'-dihydroxydiphenylsulfone is formed in a greater amount than 2,4'-dihydroxydiphenylsulfone.

In the reaction of phenol and sulfuric acid, a phosphorus compound such as phosphonic acid, phosphinic acid and phosphoric acid may be present. When the phosphorus compound is present, the content of 2,4'-dihydroxydiphenylsulfone in the formed mixture of the isomers of dihydroxydiphenylsulfone can be increased. In general, the reaction mixture obtained by the reaction of phenol and sulfuric acid contains phenolsulfonic acid in an amount corresponding to an yield of 10 to 30% based on the amount of sulfuric acid.

As for the solubility of a mixture of the isomers of dihydroxydiphenylsulfone having a content of 4,4'-dihydroxydiphenylsulfone greater than the content of 2,4'-dihydroxydiphenylsulfone in a mixed solvent of phenol and water or in phenol, the solubility of 4,4'-dihydroxydiphenylsulfone is smaller than the solubility of 2,4'-dihydroxydiphenylsulfone when the ratio of the amount by weight of phenol to the amount by weight of water is 70:30 or greater.

Figure 1:
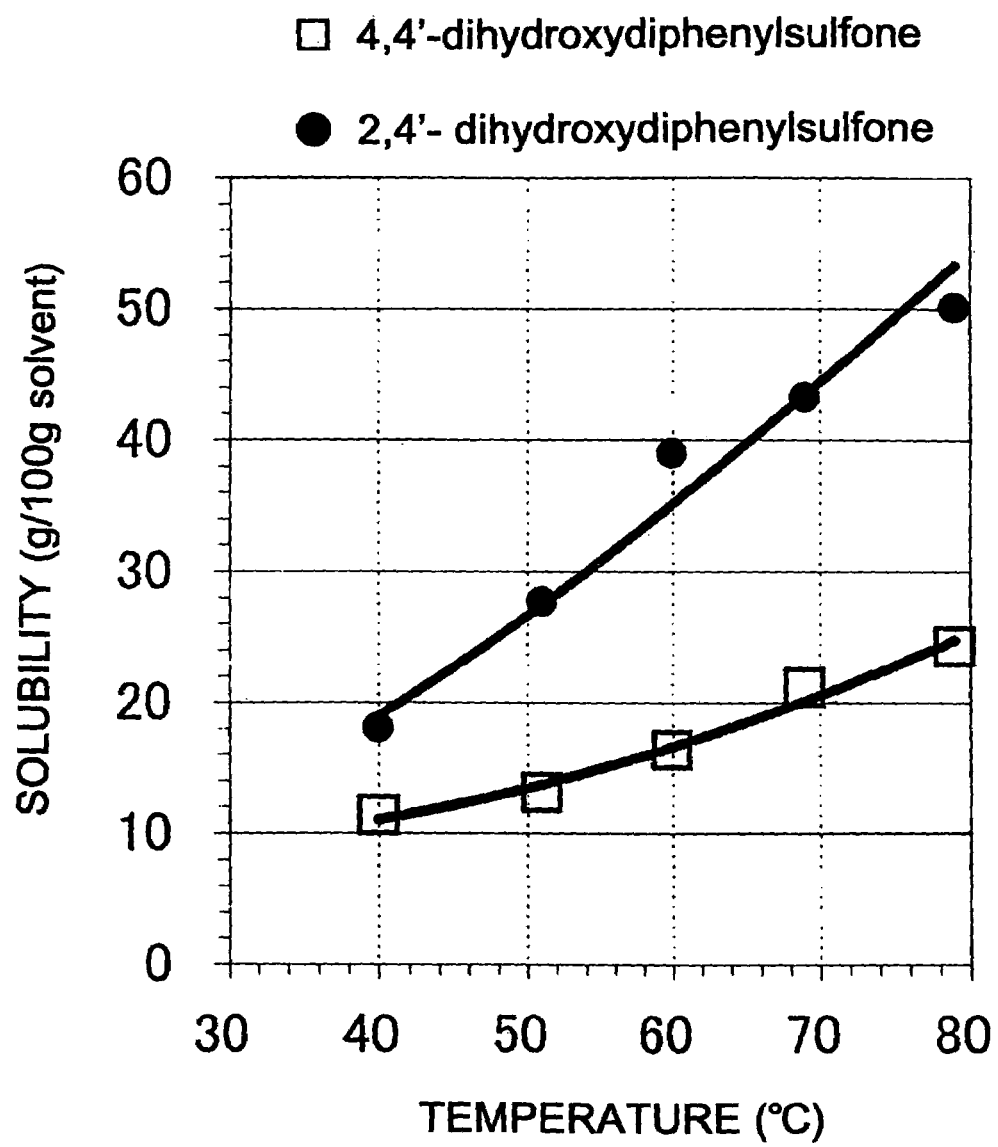
FIG. 1 shows a diagram exhibiting a solubility curve of a mixture of isomers of dihydroxydiphenylsulfone.

FIG. 1 shows a diagram exhibiting the relation between the temperature and the solubilities of the isomers in phenol when 4,4'-dihydroxydiphenylsulfone and 2,4'-dihydroxydiphenylsulfone are present in amounts such that the ratio of the amounts by weight is 50:50. Therefore, 4,4'-dihydroxydiphenylsulfone can be selectively separated by the crystallization treatment of the reaction mixture obtained by the dehydration of phenol and sulfuric acid and/or phenolsulfonic acid using a mixed solvent containing phenol and water in amounts such that the ratio of the amounts is 70:30 or greater or using phenol.

Since almost no water is contained in the reaction mixture, it is preferable that 4,4'-dihydroxydiphenylsulfone is separated by crystallization by adding phenol to the reaction mixture. The amount of the crystallized 4,4'-dihydroxydiphenylsulfone to provide the content of 2,4'-dihydroxydiphenylsulfone greater than the content of 4,4'-dihydroxydiphenylsulfone in the filtrate obtained by the crystallization of 4,4'-dihydroxydiphenylsulfone, followed by the filtration, can be calculated, and the amount of the added phenol can be obtained based on the solubility using the amount obtained by the calculation. The filtrate having a content of 2,4'-dihydroxydiphenylsulfone greater than the content of 4,4'-dihydroxydiphenylsulfone can be obtained as follows: phenol is added to the reaction mixture; the resultant mixture is heated until the entire fluid becomes homogeneous; the heated fluid is cooled, and crystals of 4,4'-dihydroxydiphenylsulfone are allowed to grow sufficiently and then separated by filtration. Since the crystals of 4,4'-dihydroxydiphenylsulfone separated by the filtration contains phenol and phenolsulfonic acid, it is preferable that the crystals are washed with hot water and dried. The obtained 4,4'-dihydroxydiphenylsulfone has a purity of 95% by weight or greater.

Figure 2:
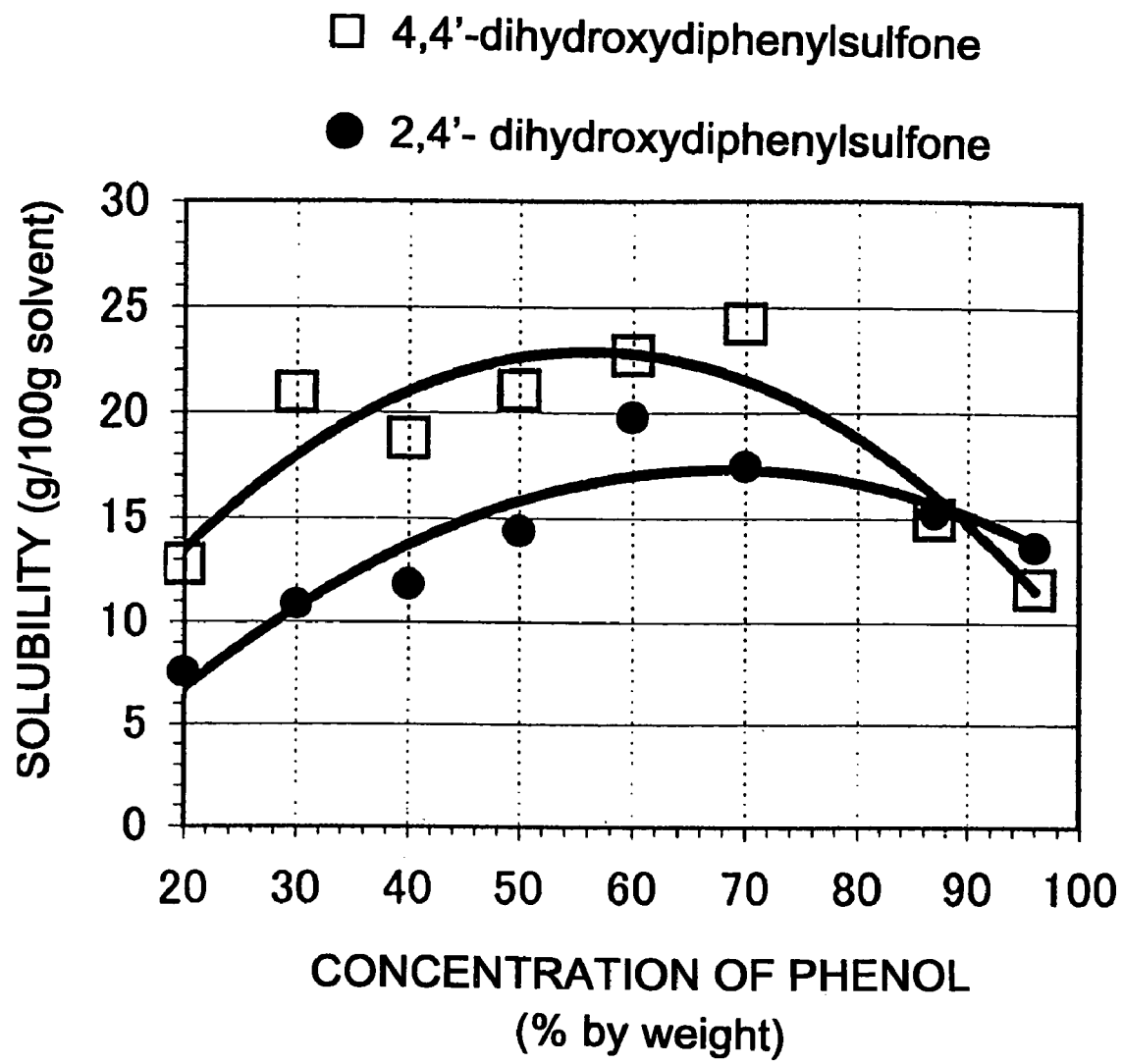
FIG. 2 shows a diagram exhibiting a solubility curve of a mixture of isomers of dihydroxydiphenylsulfone.

In the filtrate having a content of 2,4'-dihydroxydiphenylsulfone greater than the content of 4,4'-dihydroxydiphenylsulfone which is obtained by the filtration, the solvent is adjusted to have a composition such that the ratio of the amount by weight of phenol to the amount by weight of water is in the range of 10:90 to 90:10. FIG. 2 shows a diagram exhibiting the relation between the composition of the solvent and the solubilities of the isomers at 30° C. when 4,4'-dihydroxydiphenylsulfone and 2,4'-dihydroxydiphenylsulfone are present in amounts such that the ratio of the amounts by weight is 50:50. The composition and the amount of the solvent necessary for selectively crystallizing 2,4'-dihydroxydiphenylsulfone can be obtained by calculation based on the relation between the composition of the solvent and the solubilities of the isomers. It is preferable that the ratio of the amounts by weight of phenol and water is selected so that the solvent has the composition giving a small solubility of 2,4'-dihydroxydiphenylsulfone and a great difference between the solubilities of 4,4'-dihydroxydiphenylsulfone and 2,4'-dihydroxydiphenylsulfone. In general, the composition and the amount of the solvent can be adjusted by removing phenol contained in the filtrate by distillation and adding water. It is preferable that the removal of phenol from the filtrate by distillation is conducted under a reduced pressure at a temperature of 120° C. or lower. When the temperature exceeds 120° C., there is the possibility that the dehydration takes place between phenol and phenolsulfonic acid and 4,4'-dihydroxydiphenylsulfone is formed.

After the composition and the amount of the solvent are adjusted by removing phenol by distillation and adding water, the mixture is heated until the entire fluid becomes homogeneous, and the crystals of 2,4'-dihydroxydiphenylsulfone are then selectively separated by cooling, followed by filtration. It is preferable that the temperature obtained by the cooling is around the room temperature. When the temperature is excessively low during the operation of the filtration, there is the possibility that 4,4'-dihydroxydiphenylsulfone is crystallized to decrease the purity of crystals of 2,4'-dihydroxydiphenylsulfone, and the filtration becomes difficult due to the muddy condition of the mixture. It is preferable that the crystals separated by the filtration are washed with water and dried since the crystals contain phenol and phenolsulfonic acid. The obtained 2,4'-dihydroxydiphenylsulfone has a purity of 85% by weight or greater.

In the process of the present invention, the filtrate obtained by the filtration to separate 2,4'-dihydroxydiphenylsulfone is used as the raw material for producing dihydroxydiphenylsulfone. Since the filtrate obtained by the filtration to separate 2,4'-dihydroxydiphenylsulfone contains phenol, phenolsulfonic acid and water, phenolsulfonic acid which is difficult to be separated is used as the raw material, and the amount of the raw material used for producing dihydroxydiphenylsulfone can be decreased. The filtrate may be used for the dehydration after water is removed by distillation and then phenol and sulfuric acid are added. Alternately, phenol and sulfuric acid may be added to the filtrate, and the resultant mixture is heated to remove water contained in the filtrate by distillation together with water formed by the dehydration.

The mixture containing 4,4'-dihydroxydiphenylsulfone, 2,4'-dihydroxydiphenylsulfone, phenolsulfonic acid and phenol which is obtained by adding phenol and sulfuric acid to the filtrate formed by filtration of 2,4'-dihydroxydiphenylsulfone, followed by the dehydration of the resultant mixture, can be treated in the same manner as that in the treatments of the mixture containing 4,4'-dihydroxydiphenylsulfone, 2,4'-dihydroxydiphenylsulfone, phenolsulfonic acid and phenol which is obtained by the dehydration of phenol and sulfuric acid. 4,4'-Dihydroxydiphenylsulfone is separated by crystallization to obtain a mixture having a content of 2,4'-dihydroxydiphenylsulfone greater than the content of 4,4'-dihydroxydiphenylsulfone. 2,4'-Dihydroxydiphenylsulfone is crystallized by adjusting the composition of the mixture so that the ratio of the amounts by weight of phenol to water is in the range of 10:90 to 90:10; and the formed crystals are separated by filtration. The filtrate formed above by the filtration and containing phenol and phenolsulfonic acid can be used repeatedly as the raw material for producing dihydroxydiphenylsulfone by the dehydration of phenol and sulfuric acid and/or phenolsulfonic acid.

In accordance with the process of the present invention, 4,4'-dihydroxydiphenylsulfone and 2,4'-dihydroxydiphenylsulfone which are industrially useful can be separated from the reaction mixture without using specific solvents or chemicals, and the unreacted phenolsulfonic acid contained in the reaction mixture can be used as the raw material for the dehydration and effectively utilized. In the process of the present invention, since phenol which is one of the solvents used for separation of 4,4'-dihydroxydiphenylsulfone and 2,4'-dihydroxydiphenylsulfone is the raw material used for producing dihydroxydiphenylsulfone, and water which is the other solvent is a byproduct formed in the production of dihydroxydiphenylsulfone, the process of the present invention requires no additional apparatuses for recovery or purification and can be conducted economically.

EXAMPLES

The present invention will be described more specifically with reference to examples in the following. However, the present invention is not limited to the examples.

The contents of 4,4'-dihydroxydiphenylsulfone, 2,4'-dihydroxydiphenylsulfone, phenolsulfonic acid and phenol were determined in accordance with the high performance liquid chromatography.

Example 1

Into a reactor, 1,296 g of phenol, 529 g of sulfuric acid and 38 g of phosphonic acid were placed, and the dehydration was conducted under a reduced pressure of 74.6 to 34.7 kPa at 150 to 165° C. for 6 hours. The amount of the distillate of a mixture composed of phenol and water during the reaction was 547 g.

Into the reactor, 267 g of phenol was added, and the dehydration was conducted under a reduced pressure of 34.7 to 13.3 kPa for 2 hours. The amount of the entire distillate was 675 g. Then, 267 g of phenol was added into the reactor and the dehydration was conducted under a reduced pressure of 34.7 to 13.3 kPa for 2 hours. The amount of the entire distillate was 806 g. Then, 267 g of phenol was added into the reactor, and, after the dehydration was conducted under a reduced pressure of 34.7 to 13.3 kPa for 2 hours, the reaction was completed. The amount of the entire distillate was 913 g.

The amount of the obtained reaction mixture was 1,751 g, and the contents of the non-volatile components in the obtained reaction mixture were as follows: 4,4'-dihydroxydiphenylsulfone: 44% by weight; 2,4'-dihydroxydiphenylsulfone: 20% by weight; phenolsulfonic acid: 10% by weight; phenol: 24% by weight; and other components: 2% by weight. The yield of the dihydroxydiphenylsulfones based on the sulfuric acid used as the raw material was 82%.

To 1,751 g of the reaction mixture obtained above by the dehydration, 683 g of phenol was added, and the resultant mixture was heated at 120° C. so that the entire fluid became homogeneous. The temperature of the mixture in the homogeneous condition was slowly lowered to 60° C. The mixture was kept being stirred at 60° C. for 1 hour, and crystals of 4,4'-dihydroxydiphenylsulfone were allowed to grow. The formed crystals were separated by filtration, washed with water and dried, and 629 g of crystals of 4,4'-dihydroxydiphenylsulfone were obtained. The purity of the obtained crystals was 95% by weight. By the filtration, 1,767 g of a filtrate was obtained. The ratio of the amounts by weight of 4,4'-dihydroxydiphenylsulfone to 2,4'-dihydroxydiphenylsulfone was 35:65.

After 865 g of phenol was removed from the filtrate under a reduced pressure at 120° C. or lower, 515 g of water was added, and the ratio of the amounts by weight of phenol to water was adjusted at 30:70. The resultant mixture was heated at 90° C. so that the entire fluid became homogeneous. The temperature of the mixture in the homogeneous condition was slowly lowered to 30° C., and crystals of 2,4'-dihydroxydiphenylsulfone were formed. The formed crystals were separated by filtration, washed with water and dried, and 274 g of crystals of 2,4'-dihydroxydiphenylsulfone were obtained. The purity of the obtained crystals was 85% by weight. A filtrate in an amount of 1,034 g was obtained by the filtration.

Example 2

The filtrate obtained by separation of crystals of 2,4'-dihydroxydiphenylsulfone by filtration in Example 1 in an amount of 1,034 g was concentrated by removing 497 g of a mixture of water and phenol by distillation under a reduced pressure at 120° C. or lower. The concentration of phenol in the distillate was 12% by weight. The amount of the concentrated filtrate was 538 g, and the contents of non-volatile components in the concentrated filtrate were as follows: 4,4'-dihydroxydiphenylsulfone: 25% by weight; 2,4'-dihydroxydiphenylsulfone: 13% by weight; phenolsulfonic acid: 25% by weight; phenol: 25% by weight; and other components: 12% by weight.

Into a reactor, 359 g of the concentrated filtrate obtained above, 1,200 g of phenol, 432 g of sulfuric acid and 16 g of phosphonic acid were placed, and the dehydration was conducted under a reduced pressure of 74.6 to 34.7 kPa at 150 to 165° C. for 6 hours. The amount of the distillate of a mixture composed of phenol and water during the reaction was 547 g.

Into the reactor, 267 g of phenol was added, and the dehydration was conducted under a reduced pressure of 34.7 to 13.3 kPa for 2 hours. The amount of the entire distillate was 671 g. Then, 267 g of phenol was added into the reactor, and the dehydration was conducted under a reduced pressure of 34.7 to 13.3 kPa for 2 hours. The amount of the entire distillate was 810 g. Then, 267 g of phenol was added into the reactor, and, after the dehydration was conducted under a reduced pressure of 34.7 to 13.3 kPa for 2 hours, the reaction was completed. The amount of the entire distillate was 960 g.

The amount of the obtained reaction mixture was 1,846 g, and the contents of the non-volatile components in the obtained reaction mixture were as follows: 4,4'-dihydroxydiphenylsulfone: 43% by weight; 2,4'-dihydroxydiphenylsulfone: 19% by weight; phenolsulfonic acid: 8% by weight; phenol: 27% by weight; and other components: 3% by weight.

The reaction mixture obtained by the dehydration in an amount of 1,846 g was treated in accordance with the same procedures as those conducted in Example 1, and 601 g of crystals of 4,4'-dihydroxydiphenylsulfone having a purity of 95% by weight and 223 g of crystals of 2,4'-dihydroxydiphenylsulfone having a purity of 90% by weight were obtained.

Example 3

The same procedures as those conducted in Example 1 were conducted, and crystals of 4,4'-dihydroxydiphenylsulfone were separated by filtration. A filtrate containing 4,4'-dihydroxydiphenylsulfone and 2,4'-dihydroxydiphenylsulfone in amounts such that the ratio of the amount by weight was 35:65 was obtained in an amount of 1,758 g.

After 718 g of phenol was removed by distillation under a reduced pressure at 120° C. or lower from the obtained filtrate, 368 g of water was added to adjust the composition of the solvent in the mixture so that the ratio of the amounts by weight of phenol to water was 50:50. The resultant mixture was heated at 90° C. so that the entire fluid became homogeneous. The temperature of the mixture in the homogeneous condition was slowly lowered to 30° C., and crystals of 2,4'-dihydroxydiphenylsulfone were formed. The formed crystals were separated by filtration, washed with water and dried, and 262 g of 2,4'-dihydroxydiphenylsulfone was obtained. The purity of the obtained crystals was 86% by weight.

INDUSTRIAL APPLICABILITY

In accordance with the process of the present invention, highly pure 2,4'-dihydroxydiphenylsulfone can be obtained from a mixture of 4,4'-dihydroxydiphenylsulfone and 2,4'-dihydroxydiphenylsulfone easily with a great yield without using organic solvents or a great amount of an acid or an alkali. Unreacted phenolsulfonic acid contained in the filtrate obtained by filtration of 2,4'-dihydroxydiphenylsulfone can be used as a portion of the raw materials in the next reaction, and the amount of the raw materials in the production of 2,4'-dihydroxydiphenylsulfone can be decreased.

The invention claimed is:

1. A process for producing 2,4'-dihydroxydiphenylsulfone which comprises separating 4,4'-dihydroxydiphenylsulfone by crystallization from a mixture comprising 4,4'-dihydroxydiphenylsulfone, 2,4'-dihydroxydiphenylsulfone, phenolsulfonic acid and phenol which is obtained by dehydration of phenol and sulfuric acid or phenolsulfonic acid so that a mixture having a content of 2,4'-dihydroxydiphenylsulfone greater than a content of 4,4'-dihydroxydiphenylsulfone is obtained, crystallizing 2,4'-dihydroxydiphenylsulfone by adjusting a composition of a solvent of an obtained mixture so that a ratio of an amount by weight of phenol to an amount by weight of water is in a range of 10:90 to 90:10, and separating 2,4'-dihydroxydiphenylsulfone by filtration.

2. A process for producing 2,4'-dihydroxydiphenylsulfone according to claim 1, which comprises adding phenol and sulfuric acid to a filtrate obtained by the separation of 2,4'-dihydroxydiphenylsulfone by filtration, conducting dehydration using a resultant mixture, separating 4,4'-dihydroxydiphenylsulfone by crystallization from a product of dehydration comprising 4,4'-dihydroxydiphenylsulfone, 2,4'-dihydroxydiphenylsulfone, phenolsulfonic acid and phenol so that a mixture having a content of 2,4'-dihydroxydiphenylsulfone greater than a content of 4,4'-dihydroxydiphenylsulfone is obtained, crystallizing 2,4'-dihydroxydiphenylsulfone by adjusting a composition of a solvent of an obtained mixture so that a ratio of an amount by weight of phenol to an amount by weight of water is in a range of 10:90 to 90:10, and separating 2,4'-dihydroxydiphenylsulfone by filtration.

* * * * *